United States Patent [19]

Hurwitz

[11] 4,252,022
[45] Feb. 24, 1981

[54] DETECTION, CHARACTERIZATION AND STUDYING OF FLAWS IN WORK BY ACOUSTIC IMAGING

[75] Inventor: Michael J. Hurwitz, Pittsburgh, Pa.

[73] Assignee: Westinghouse Electric Corp., Pittsburgh, Pa.

[21] Appl. No.: 961,787

[22] Filed: Nov. 17, 1978

[51] Int. Cl.$^2$ .......................................... G01N 29/04
[52] U.S. Cl. ...................... 73/582; 73/598; 73/633; 73/644
[58] Field of Search ............... 73/620, 622, 633, 644, 73/598, 582

[56] References Cited

U.S. PATENT DOCUMENTS

| | | | |
|---|---|---|---|
| 3,781,576 | 12/1973 | Runde et al. | 73/644 |
| 4,010,635 | 3/1977 | Patsey | 73/644 |

FOREIGN PATENT DOCUMENTS

738941  10/1955  United Kingdom ...................... 73/644

*Primary Examiner*—Anthony V. Ciarlante
*Attorney, Agent, or Firm*—D. C. Abeles

[57] ABSTRACT

In detecting, characterizing or studying flaws in work whose surface is irregular by acoustic imaging in which a holographic pattern is produced the irregular surface is scanned by acoustic energy focussed on or near the irregular surface and the reception of the acoustic energy resulting from echoes from flaws is controlled for each scanned elemental area so as to reduce to a negligible magnitude the effects or variations in the acoustical path caused by the irregularties at different elemental areas in accordance with the irregularity at that area. The control may be effected by filling in the depressions in the irregular surface with an acoustic energy absorbing material such as butyl rubber or with a material, such as wax, which is not wetted by the liquid through which the acoustic energy is propagated to the surface. The control may also be effected by introducing a phase-shift correction into the reference frequency signal, the electrical analog of an acoustical reference wave, which cooperatively with the signal derived from the received acoustic energy produces the interference pattern on the hologram.

10 Claims, 8 Drawing Figures

DETECTION, CHARACTERIZATION AND STUDYING OF FLAWS IN WORK BY ACOUSTIC IMAGING

REFERENCE TO RELATED DOCUMENTS

This application relates to and incorporates by reference application Ser. No. 961,788, filed concurrently herewith to Michael J. Hurwitz for "Flaw Detection, Characterization And Study" (herein called Hurwitz application) and assigned to Westinghouse Electric Corporation.

BACKGROUND OF THE INVENTION

This invention relates to flaw detection, characterization and studying by acoustic imaging and has particular relationship to such flaw detection and characterization where the surface of the work or specimen under observation is irregular.

Flaw detection by acoustic imaging is used in the inspection of nuclear reactor pressure vessels. In this area acoustic imaging helps to characterize the flaws or defects precisely enough so that, by fracture mechanics, the defects can be reliably estimated. Nuclear reactor pressure vessels are clad with stainless steel or other usually ferrous anti-corrosion material. The cladding is usually deposited by arc welding and the surface of the cladding is irregular. The irregularities vary the acoustic path of the energy which is propagated during the imaging and deteriorate the reliability of the results.

As disclosed in Hurwitz application, in acoustic imaging, acoustic energy from an acoustic lens or a focussed-arc transducer submerged in a liquid, typically water, is propagated to the work and scans the work through the liquid. The resulting acoustic-energy echoes received from defects of flaws are processed electronically and optically to produce an acoustic pattern from which the flaws may be characterized. This invention predominately concerns itself with acoustic imaging in which acoustic energy is focussed on or near the surface of the work by an acoustic-lens transducer and produces or stores a holographic pattern. Where clad work is inspected, the acoustic energy is focussed on or near the irregular surface. This invention is uniquely applicable to holographic presentation but in its ramifications it may be applicable to other forms of presentations. To the extent that this invention is so applicable, such use is within the scope of this application or of any patent which may issue on or as a result thereof.

For an understanding of the influence, on acoustic imaging, of irregularities in the surface of the work impinged by the acoustic energy, it is necessary that the effect of the irregularities on the acoustic path length be determined. If this effect were negligible, no problem would be confronted. In fact, under the conditions under which acoustic imaging is carried out, the effect is appreciable and may at times be devastating.

Typically, the frequency of the acoustic energy is 4 megahertz for which the wavelength $\lambda_1 = 0.015$ inch in water. The liquid through which the propagation of acoustic energy takes place is assumed to be water. The ratio of the sound velocity in alloys such as stainless steel to that in water is 4:1. As in optical imaging, acoustic imaging can tolerate random phase errors of only $\frac{1}{8}$ to $\frac{1}{4}$ the wavelength. Because of the high ratio of sound velocity and because of the short wavelength of the acoustic energy, small irregularities in the surface of the work can drastically change the acoustic-path length, in terms of wavelengths, over different parts of the scanned raster.

For acoustic energy impinging on a water-steel interface at normal incidence, the acoustic path-length P in numbers of wavelength is, to a first approximation, defined by the equation:

$$P = \frac{D_1}{\lambda_1} + \frac{D_2}{\lambda_2} \tag{1}$$

where:

$D_1$ is the actual distance traversed by the acoustic energy in water;

$D_2$ is the actual distance traversed by the acoustic energy in steel;

$\lambda_1$ is the wavelength of the acoustic energy in water; and $\lambda_2$ is the wavelength of the acoustic energy in steel.

Let $D = D_1 + D_2$; D is a constant.

$$P = \frac{D_1}{\lambda_1} + \frac{(D - D_1)}{\lambda_2} \tag{2}$$

$$n_1 \lambda_1 = n_2 \lambda_2$$

where:

$n_1$ is the index of refraction in water;

$n_2$ is the index of refraction in steel.

$$\lambda_2 = \frac{n_1 \lambda_1}{n_2}$$

$$n_1 = 1$$

$$P = \frac{D_1}{\lambda_1} + \frac{n_2(D - D_1)}{\lambda_1} \tag{3}$$

$$\frac{dP}{dD_1} = \frac{(1 - n_2)}{\lambda_1} \tag{4}$$

$$\Delta P = \frac{(1 - n_2)\Delta D_1}{\lambda_1} \tag{5}$$

where $\Delta P$ is an increment in path length produced by an increment in travel distance in medium 1, the water.

For a water to steel interface; using a frequency of 4 MHz $$n_2 = 0.25, \lambda_1 = 0.015.$$

For an allowable path length error of $\frac{1}{4}$ wavelength, equation (5) becomes $$\frac{1}{4} = \frac{.75}{.015} \Delta D.$$

$$\Delta D_1 = .005 \text{ inch.}$$

It appears then, in the case of a randomly irregular surface, that if the root-mean-square random ripple of the surface ($D_1$) is of the order of 0.005 inch, the acoustic images are destroyed. If the surface irregularities are systematic, for example of spherical or cylindrical curvature or in steps, larger errors than $\frac{1}{4}$ wavelength can be tolerated. Such irregularities produce correctable distortions but do not destroy the images. In fact, random fluctuations whose roughness is about 10 times the 0.005 permissible roughness occur in the surface of the cladding for some nuclear reactor vessels.

It is an object of this invention to produce clear, well-defined, undistorted images, particularly holographic reconstructed images, by acoustic imaging to achieve reliable detection and characterization of flaws in work such as the cladding of nuclear reactor vessels, notwithstanding the irregularity of the surface scanned by the acoustic energy.

SUMMARY OF THE INVENTION

An aspect of this invention arises from the observation that in many cases the high areas of the cladding, i.e., the areas facing the scanning means, are predominately flat while the depressions are sharply curved. In addition, it has been realized that acoustic energy impinging and focussed on or near an element of a surface through which it penetrates, diverges within the work below the element as it is propagated. Such diverging energy reflects echoes from any flaws below the element which may be displaced laterally of the element. The acoustic energy echoes can then penetrate through elements of the surface along the path through which they entered to yield signals characterizing the flaws.

In accordance with an aspect of this invention, the depressions of the irregular surface on or near which the acoustic energy is to be focussed and which is to be scanned by the focussed acoustic energy are filled in with an acoustic-energy absorption material. Typical of such material are elastomers such as butyl rubber or silicone rubber. The incident acoustic energy is then propagated into the material through the high-point areas which are at substantially the same level and the acoustic energy echoes are propagated to the receiving transducers through the same high-point areas. The acoustic path in wavelengths of the acoustic energy then remains substantially constant. The same result is achieved by filling the depressions with a material, which reflects acoustic energy such as wax, which is not wetted by the water. The acoustic energy cannot penetrate through the gap between the water and the non-wetted material. It is then propagated back and forth through the high areas of the surface.

Where acoustic energy echoes passing through patches of the surface of the work of one to two wavelength diameter are separable, corrections for the irregularities may be effected by scanned transmit-receive acoustical holography. This correction is effected elemental area by elemental area. Where the acoustic-energy frequency is 4 megahertz, a one to two wavelength diameter path has a diameter of 0.015 to 0.030 inch in water. The scanning may take place, as disclosed in Hurwitz application, by scanning movement in both dimensions, over elemental areas one by one by an acoustic-lens transducer, which focusses the acoustic energy on or near the irregular surface. It may also take place by scanning in one dimension of a linear array of small focussing transducer elements which focus their respective acoustic energy on or near the irregular surface. These elements are enabled in sequence so that the signals from elemental areas are separated. The scanning may also be carried out by a two-dimensional array of small transducer elements which focus their respective acoustic energy on the irregular surface and are enabled in a predetermined sequence. Detailed consideration will here be given to the method of scanning disclosed in Hurwitz application.

In this case, a small acoustic focal spot scans the irregular surface of the work which may be several square inches in area or larger. Typically, the acoustic lens transducer is spaced about 2 to 6 inches from the scanned surface. Variations in $D_1$, the water-path distance, by reason of surface irregularities of the work, can be measured by measuring, for each elemental area, the time between the transmission of the acoustic-energy pulse and the receipt of the first echo from this pulse. The first echo is the echo reflected from the interface of the water and the irregular surface, as distinct from the later echo reflected from a flaw. This time, t, is given by:

$$t = 2D_1/C_\omega \quad (6)$$

where $C_\omega$ is the velocity of the acoustic energy in water.

$$\Delta t = \frac{2\Delta D_1}{C_\omega} \quad (7)$$

$$\Delta D_1 = \frac{C_\omega \Delta t}{2} \quad (8)$$

$\Delta D_1$ for different elemental areas can readily be measured.

According to equation (5)

$$\Delta P = (1 - n_2) \frac{\Delta D_1}{\lambda_1} \quad (5)$$

$$\Delta P = \frac{(1 - n_2)}{\lambda_1} \frac{C_\omega \Delta t}{2} \quad (9)$$

$$\Delta P = \frac{(1 - n_2)}{2} f \Delta t \quad (10)$$

where f is the frequency of the acoustic energy.

Where $n_2 = 0.25$, as for steel, $$p = 0.375 f \Delta t \quad (11)$$

Equation (11) converts $\Delta t$ into a phase variation $\Delta P$. The acoustic imaging is deleteriously affected when $\Delta P$ is of the order of ¼ of a cycle or greater.

In accordance with this aspect of the invention, the correction for irregularities is effected by advancing or retarding the phase of the electrical analogy of the acoustical reference wave, which in cooperation with the received signal, produces the holographic interference pattern (i.e., the hologram) in dependence upon the irregularities of the incident surface.

With the interference pattern so corrected, reconstruction of the holographic interference pattern with a laser beam yields a reliable well defined image free of distortions showing the flaws in the work.

The above-described practice of this invention is straightforward when there can be established a hypothetical reference plane through the irregular surface which is parallel to the surface traced by the focal point of the acoustic beam. If no such reference plane can be established, it is necessary to determine the time variation by reference to other surfaces than the parallel reference plane. Such other reference surface is determined statistically by recording holographic information and times of return of the first echo, the echo from the interface of the water and metal, in a quickly retrievable memory, for example, a tape, magnetic video disc recorder, or digital computer memory. This information is fed to a digital computer which determines statistically (by least squares, for example) the best reference plane or other reference surface (e.g., spherical, cylindrical). This reference surface yields anticipated times of return of the first echoes from the elemental areas of the surface of the work after transmission of the pulses. The times of return, $\Delta t$, and $\Delta P$ can then be determined by subtracting the actual times of return of the first echoes from the anticipated times of return and introducing the difference as a correction into the holographic process as an analog or digitally.

By noting the Δt's, a determination can be made whether or not an area of a surface of a specimen is sharply curved. If there is sharp curvature, there may be pronounced refraction of the acoustic energy at the interface of the water and the surface of the work. In this case, it is preferred that the echo signals from the sharply curved regions be deleted if adequate intelligence can be derived from the remainder of the surface.

BRIEF DESCRIPTION OF THE DRAWINGS

For a better understanding of this invention, both as to its organization and as to its method of operation, together with additional objects and advantages thereof, reference is made to the following description, taken in connection with the accompanying drawings, in which.

Figure 5:
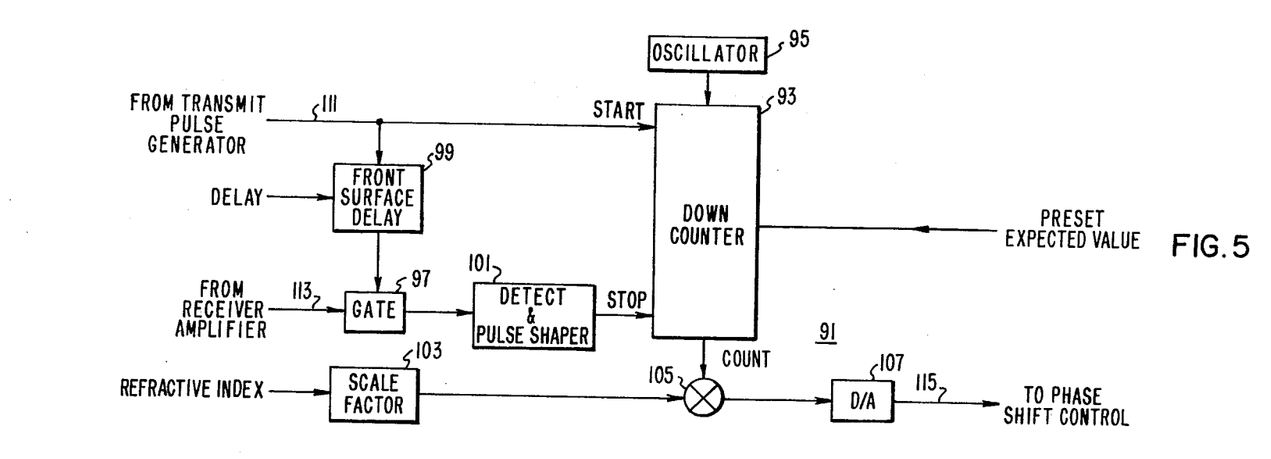
FIG. 5 is a block diagram showing the manner in which a correction signal for irregularities in the surface of work is derived in the practice of an aspect of this invention.
Figure 6:
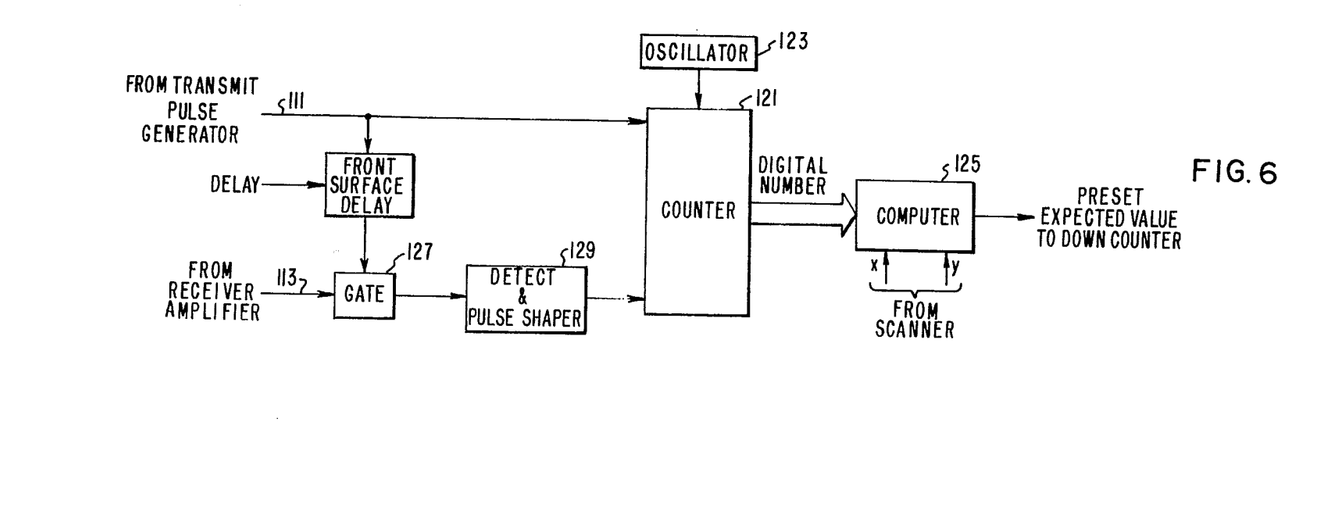
FIG. 6 is a block diagram showing the manner in which reference surface data is derived where the reference surface is a plane at an angle to the plane scanned by the focal point of the acoustic energy.
Figure 8:
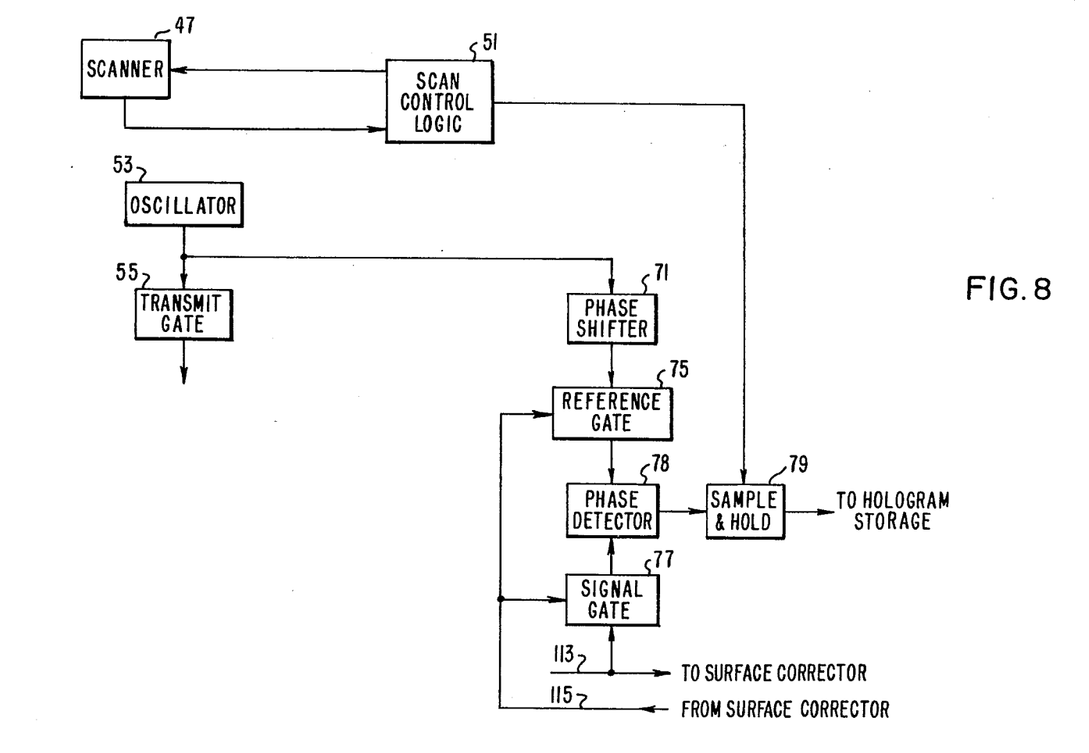
FIG. 8 is a block diagram of a holographic electronic subassembly illustrating another aspect of this invention.

The blocks in FIGS. 5, 6, and 8 correspond to functions of the apparatus and do not necessarily represent separate structural components of the apparatus. The functions may be performed by parts of a solid-state assembly or bits of a computer which are not physically separable.

DESCRIPTION OF THE PREFERRED EMBODIMENTS

Figure 1:
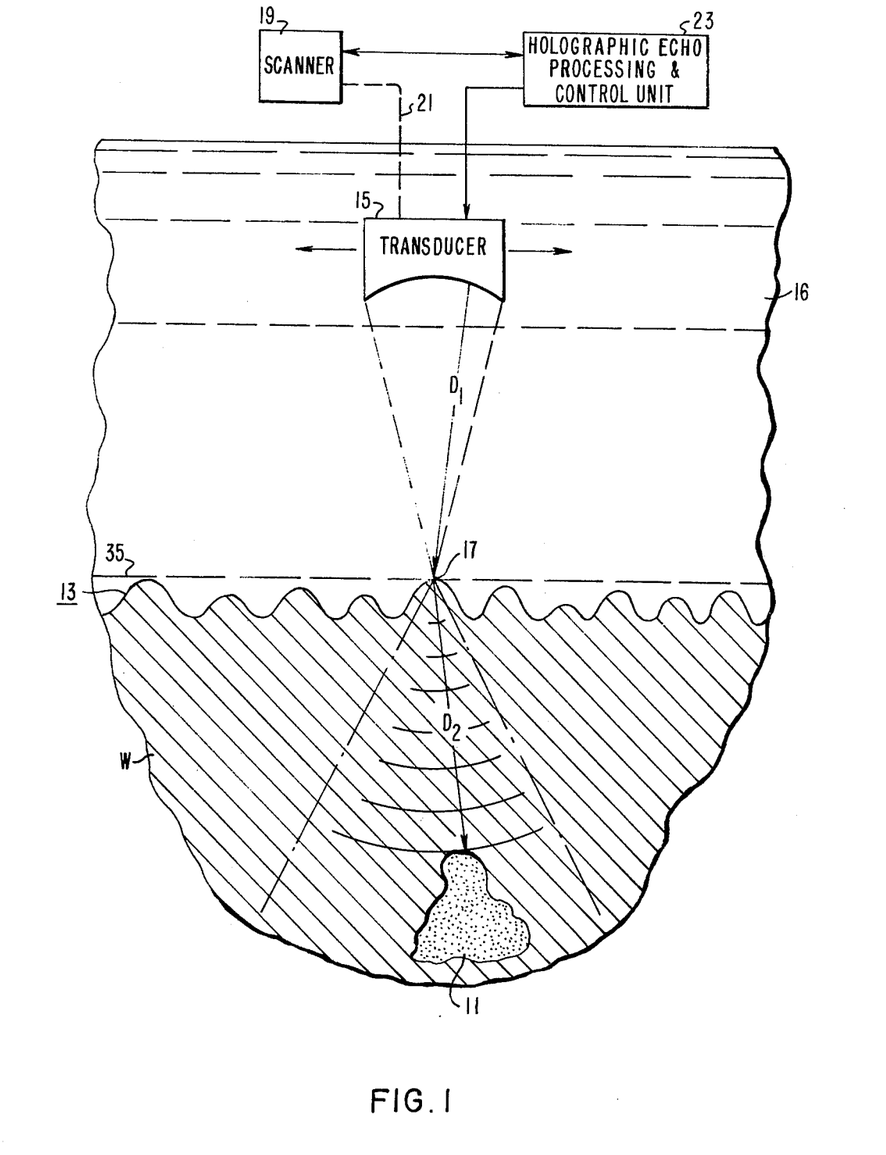
FIG. 1 is a diagrammatic view in the form of a block diagram illustrating the general practice of this invention.

FIG. 1 illustrates the practice of this invention in detecting a flaw 11 in work W which has an irregular surface 13 on which acoustic energy impinges. The work W is submerged under water 16. Acoustic energy from an acoustic lens transducer 15, also submerged under water 16, focussed at a point 17 on or near the surface, scans the surface in two dimensions. The transducer 15 is moved over the surface by a scanner 19 connected to the transducer through a bar or bracket 21, as disclosed in Hurwitz application.

The apparatus shown in FIG. 1 also includes a holographic echo processing and control unit 23. This unit 23 typically includes the components disclosed in Hurwitz application or variations of these components as shown in FIGS. 4, 5, 6 and 8 of this application. The unit 23 includes a processing subassembly for transmitting acoustic energy pulses to energize the transducer 15 and for receiving acoustic energy echoes. There is also a scan-control logic (as disclosed in Hurwitz application at 34) for coordinating the scanning with the signals transmitted and received by the processing subassembly. As disclosed in Hurwitz application, the scan control logic also supplies a phase shift dependent on the scanning positions to the electrical analog of the acoustical reference wave to suppress flooding of the hologram by light or a reconstructing laser beam impressed on the hologram at right angles.

The acoustic energy from the transducer, focussed at any point 17 of the scanned raster, penetrates into the work W and is propagated through the work in waves which diverge. Waves reflected from the flaw 11 as echoes are received and processed to produce the holographic pattern. As shown in FIG. 1, and in line with the above parameter designations, the distance in water from the transducer 15 to point 17 is labelled $D_1$ and the distance in the work from the focal point 17 to the flaw boundary where the echo is reflected is labelled $D_2$.

Figure 2:
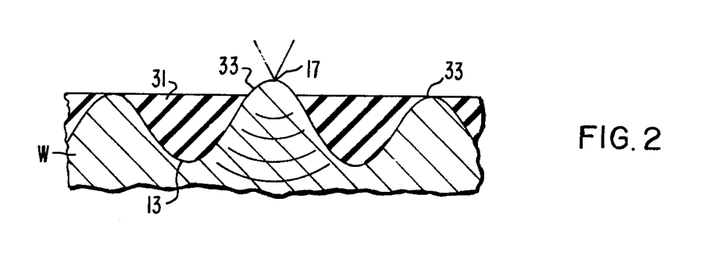
FIG. 2 is a fragmental view enlarged of a section of work illustrating an aspect of this invention.

In the practice of an aspect of this invention shown in FIG. 2, correction is effected for the irregularities in the surface 13 of the work W by filling the depressions with a material 31 which is absorptive of acoustic energy or which is not wetted by the water. In work, so treated the acoustic energy is propagated into the work W only through the high points 33 which are uncoated. As the acoustic energy is propagated through the work W, it spreads out or diverges. A flaw 11 laterally of the point of penetration reflects echoes which are processed to produce holograms that can be reconstructed. Since the high points 33 of the work W are substantially at the same level, ΔP for the echoes is substantially zero or substantially smaller than λ/8 and the reconstructed holograms are reliable and clear and yield the information sought.

Figure 3:
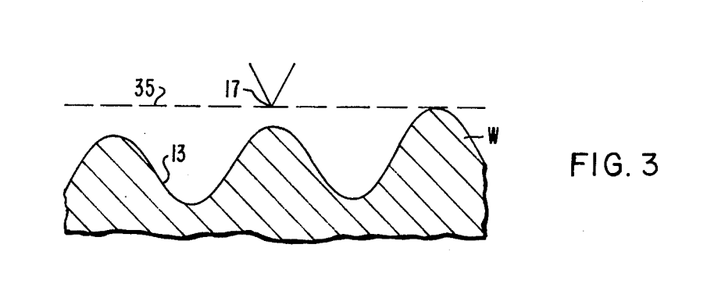
FIG. 3 is a like fragmental view enlarged of a section of work illustrating another aspect of this invention.

In accordance with another aspect of this invention, correction may be effected for the irregularities of the surface 13 of the work W by introducing electrical correcting phase increments into the electrical analog of the acoustical reference wave which is mixed with the received echo. First, it is assumed that a hypothetical plane 35 (FIGS. 1 and 3) which is parallel to the plane defined by the focal point 17 as it scans its raster can be defined. With reference to FIGS. 1 and 3, it is assumed that the plane passes through the highest peak of the surface 13. The increments, ΔP, are then measured for the elemental areas scanned from the highest peak to the surface 13 below. Corrected holograms in reliance upon plane 35 as the reference plane are produced with the apparatus shown in FIGS. 4 and 5.

Figure 4:
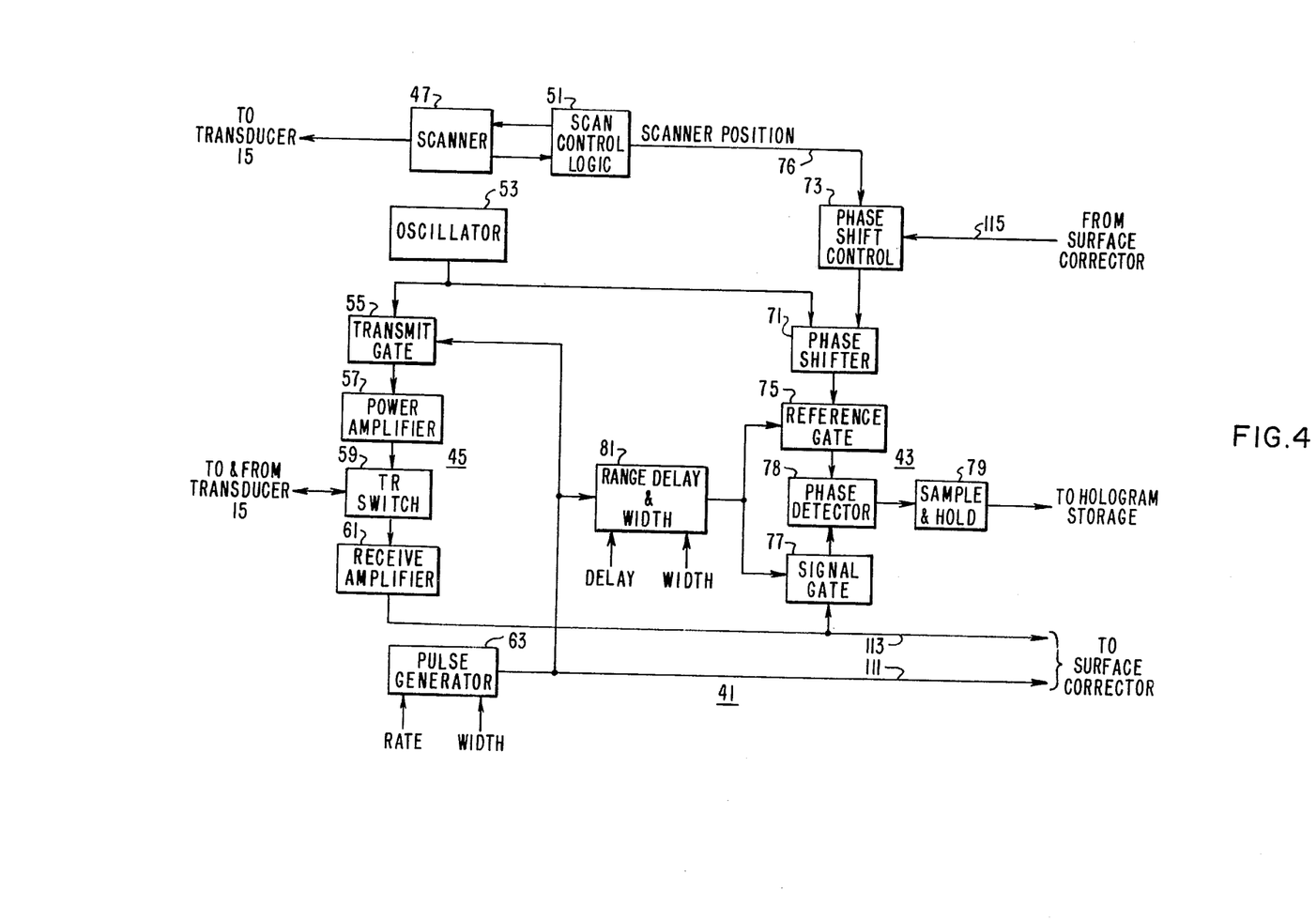
FIG. 4 is a block diagram showing a holographic echo-processing unit for practicing an aspect of this invention.

FIG. 4 shows a holographic echo-processing unit 41 including facilities for correcting, for irregularities in the surface 13, in the reference-frequency channel 43. This apparatus also includes an echo-processing subassembly 45, a scanner 47, and scan-control logic 51, as shown in Hurwitz application.

The echo-processing subassembly 45 includes an oscillator 53 (typically 4 megahertz), a transmit gate 55, a power amplifier 57, a transmit-receive switch 59 and a receiver amplifier 61. The transmit gate 55 is controlled by a pulse generator 63 which sets the duration, rate and amplitude of the pulse trains of waves, from oscillator 53, which are transmitted. The pulses are transmitted through the TR switch 59 to energize the transducer 15. The transducer 15 propagates acoustic energy to the work W. The transducer 15 is driven by the scanner 47 to scan the surface 13 of the work W. The scanner 47 is driven by pulses from the scan-control logic 51 which controls the scanner. The echoes are transmitted through the TR switch 59 to the receiver amplifier 61.

The reference frequency channel 43 includes a phase shifter 71, a phase-shift control 73, a reference gate 75, a signal gate 77, a phase detector 78, and a sample hold 79. The output of the sample hold 79 is supplied to the hologram storage which may be a film, a memory in a computer or a temporary digital buffer. The channel 43 includes a range-delay and width 81.

The oscillator 53, in addition to supplying the wave which modulates the pulses transmitted by the transducer 15, also supplies the electrical analog of the acoustical reference wave. This electrical analog is supplied through the phase shifter 71 which shifts the phase of the electrical analog in accordance with its setting. The phase shift is set by the phase shifter control 73. The phase shift which the phase shift control 73 impresses on the phase shifter 71 is made up of two components or corrections: One component derived from the scan-control logic 51, through conductor 76, and coordinated with the scanning, adjusts the phase of the electrical analog of the acoustical reference wave so as to produce a holographic interference pattern with respect to which the reconstructed image is off axis. The reconstructed image is then not flooded by the undiffracted light beam from the reconstructing laser which impinges at right angles on the interference pattern. Adjusted by this phase shift set by scan control logic 51, the phase shifter 71 produces the effect which would be produced if the laser beam were transmitted at an angle substantially different than 90° to the interference pattern (the hologram). The other component, impressed on phase shift control 73 through conductor 115, introduces phase changes into the electrical analog which correct for irregularities in the surface 13 of the work W.

The range delay and width 81 is controlled from the pulse generator 63. The pulse which passes to the transmit gate and which, modulating the waves from the oscillator 53, becomes the transmitted pulse, also controls the range delay and duration. The range delay and width 81 opens the reference gate 75 and the signal gate 77 at the appropriate time and for the appropriate duration to receive and process the acoustic-energy echo.

The reference frequency, shifted in phase as set by the phase shifter 71, is passed to the phase detector 78 by the reference gate 75, while this gate is open during the receiving interval. The signal gate 77 is connected to the receiver amplifier 61. While gate 77 is open, during the same interval as the reference gate 75, the signal gate passes the received echo signal to the phase detector 78. The phase detector passes the resulting detected signal, actually a measure of the phase displacement, to the sample and hold 79 which may be a modulated light source, as shown in Hurwitz application. The hologram is produced by the signal from the sample and hold 79 on a film or the intelligence defining the hologram is stored. On the receipt of each signal, the sample and hold 79 retains its response to the signal until it receives the next signal. The sample and hold may be a light source whose intensity varies with the received signal. In this case, the light source would hold each intensity until the next intensity is received.

FIG. 5 shows a surface corrector 91 for supplying intelligence to the phase shift control 73 (FIG. 4) to correct for irregularities in the surface 13 of the work W (FIG. 3). The surface corrector 91 includes a down counter 93 which is driven by an oscillator or clock 95. The surface corrector 91 also includes a gate 97 which is opened by a signal from a front surface delay 99. There are also a detector and pulse shaper 101, a scale factor 103, a multiplier 105 and a digital-to-analog converter 107.

A preset expected value is strobed into the down counter 93. Where the hypothetical reference plane 35 is parallel to the surface defined by the focal point 17 (FIG. 4) as it scans, the preset expected value is constant. In other cases, this value varies elemental area by elemental area in accordance with the reference surface. The down counter 93 is enabled through conductor 111 by each pulse from the pulse generator 63 (FIG. 4) when the transducer 15 is energized to transmit a pulse of acoustic energy to the work W. When so enabled, the down counter counts down. If the preset expected value is derived from a hypothetical plane 35 defined by the highest point of the surface 13, the down counter 93 counts down from this value. If the hypothetical plane 35 is a plane extending between the peaks and depressions of surface 13, the down counter counts a number of positive counts corresponding to the reference plane and then counts negative counts from the reference plane to the elemental area, if any, below the reference plane. The down counting continues until the echo from the surface 13 is received. On receipt of this echo, the down counting is stopped. The echo signal is transmitted from the receiver amplifier 61 (FIG. 4) through conductor 113. The echo signal is impressed on the down counter 93 through gate 97 and detector and pulse shaper 101. The gate 97 is opened during a short interval, during which the echo signal from the surface 13 is anticipated, by operation of front surface delay 99. The count of the down counter between the instant when the enabling pulse is impressed and the instant when the echo signal is impressed is a measure of $\Delta t$ in Equation 10. This number is transmitted to the multiplier 105 where it is multiplied by the scale factor which is proportional to $(1-n_2)/2$. The product is impressed on the digital-to-analog converter 107. The output of the digital-to-analog converter 107 is a correcting phase shift increment which is impressed on the phase shift control 73 (FIG. 4) through conductor 115. This increment is processed as described above to provide a corrected signal for the elemental area being instantaneously scanned at sample hold 79 for transmission to hologram storage.

Where the surface of the work W to which the acoustic energy is propagated is not parallel to the plane defined by focal point 17 during the scanning, the preset expected value impressed each instant on the down counter 93 varies in dependence upon the time which would be taken by a hypothetical echo to be received, from an elemental area being scanned at their instant, of the hypothetical surface which corresponds to the surface of the work. A plane hypothetical surface at an angle to the plane defined by point 17 would be defined by the equation $$T = Ax + By + K \qquad (12)$$

where T is the time taken by the hypothetical echo to be received from an elemental area of the hypothetical surface having coordinates x and y and A, B and K are constants. The best constants A, B and K can be determined and thus equation 12 quantified by a preliminary operation carried out with the apparatus shown in FIG.

6. This view includes a counter 121 which, when enabled, is actuated to count by an oscillator or clock 123. There is also a computer 125 with a memory which receives and retains counts from the counter. The counter is enabled by a pulse from the pulse generator 63 (FIG. 4) supplied through line 111. Simultaneously with the transmission of the enabling pulse, acoustic energy is transmitted to an elemental area having coordinates x and y of the work W. The echo signal received by receiver 61 (FIG. 4) is transmitted to the counter through gate 127, when the gate is opened by delay 129, and through detector and pulse shaper 131 to stop the counting. The counts for the respective elemental areas are strobed into the memory of computer 125 together with the magnitudes of the corresponding coordinates x and y. The values retained by the computer are represented in the following table.

| Time | x | y |
|---|---|---|
| $T_1$ | $x_1$ | $y_1$ |
| $T_2$ | $x_2$ | $y_2$ |
| . | . | . |
| . | . | . |
| . | . | . |
| $T_n$ | $x_n$ | $y_n$ |

Figure 7:
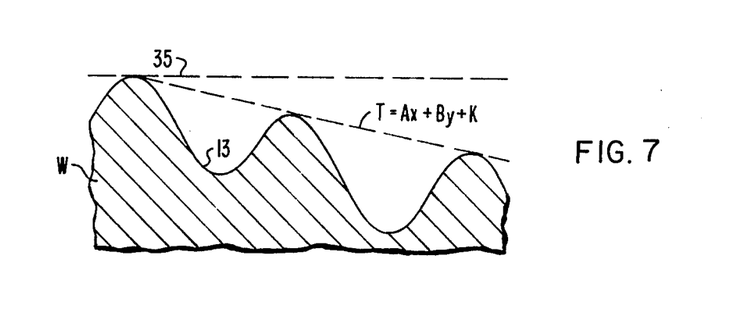
FIG. 7 is a fragmental view enlarged of a section of the work illustrating the operation of FIG. 6.

The computer 125 having magnitudes of T, x and y for a number of elemental areas of the work surface can compute A, B, and K by least-square methods and thus quantify equation 12 and determine the best hypothetical plane approximating the surface 13 of the work W. The time derived from the hypothetical plane (Equation 12) for each elemental area of the work can be strobed into down counter 93 as the preset expected value in each case. FIG. 7 shows the relationship between plane 35, the surface 13 of the work W and the plane $T = Ax + By + K$.

Another way of correcting for the irregularities is to control the signal gate 77 (FIG. 4) and the reference gate 75 from the output of the multiplier 105 (FIG. 5) so that the signal gate 77 and the reference gate 75 do not pass signals when the correcting phase shift would exceed a permissible limiting magnitude, for example $\lambda/8$. This alternative is illustrated in FIG. 8 which is similar to FIG. 4, except that it does not include the phase-shift control 73. In this case, signals received directly from the multiplier 105 or from the digital-to-analog converter 107 are impressed on the gates 75 and 77 to suppress a transmission of intelligence to sample and hold 79 when the phase shift exceeds $\lambda/8$ or a corresponding number. The alternative just described is only practicable if there are sufficient elemental areas within the $\lambda/8$ limit to provide adequate flaw echoes.

While a preferred embodiment of this invention has been disclosed herein, many modifications are feasible. This invention is not to be limited except insofar as is necessitated by the spirit of the prior art.

I claim:

1. The method of detecting, characterizing or studying flaws in work having an irregular surface by acoustic imaging, the said method comprising generating acoustic energy, from an acoustical source, focussing said acoustic energy on or near said irregular surface, scanning said surface with said focussed acoustic energy, receiving resulting acoustic energy from echoes from said flaws, controlling the reception of acoustic energy resulting from focussed acoustic energy impinging on or near each elemental area of said irregular surface, as said elemental area is scanned, in accordance with the irregularity of said surface at said elemental area so as to reduce to a negligible magnitude the effects of differences in said received acoustic energy resulting from differences in the acoustical path lengths between said source and different elemental areas of said irregular surface scanned by said focussed acoustic energy, and forming a pattern of the controlled received acoustic energy.

2. The method of claim 1 wherein the irregularities are in the form of peaks and depressions and wherein the acoustic energy, on impinging on any elemental area on or near the irregular surface, spreads out throughout the work below the surface, the said method being characterized by the step of controlling the reception of acoustic energy, in accordance with the irregularities in said surface, by filling in said depressions with a material which is highly absorptive of acoustic energy whereby echoes result only from focussed acoustic energy penetrating through said peaks.

3. The method of claim 1 wherein the irregularities are in the form of peaks and depressions, and wherein the acoustic energy is transmitted to the work through a liquid, and wherein the acoustic energy, on impinging on any elemental area on or near the irregular surface, spreads out throughout the work below the surface, the said method being characterized by controlling the reception of said acoustic energy in accordance with the irregularities, in said surface by filling in said depressions with a material which reflects said acoustic energy whereby acoustic energy echoes result only from focussed acoustic energy penetrating through said peaks.

4. The method of claim 1 whereby the irregularities of the surface are in the form of peaks and depressions and wherein the acoustic energy, on impinging on an elemental area on or near the irregular surface and being transmitted through the work, spreads out throughout the work below the surface, the said method being characterized by the step of controlling the reception of acoustic energy, in accordance with the irregularities of the surface, by filling in the depressions with a material which prevents the transmission of the focussed acoustic energy through the work, whereby echos result only from focussed acoustic energy penetrating through said peaks.

5. The method of detecting, characterizing or studying flaws in work having an irregular surface by acoustic imaging, the said method comprising generating acoustic energy, from an acoustic energy source, focussing said acoustic energy on or near said irregular surface, scanning said surface with said focussed acoustic energy, receiving resulting acoustic energy from echoes from said flaws, converting said received acoustic energy into electrical signals, modifying the signals converted from focussed acoustic energy impinging on or near each elemental area of said irregular surface, as said elemental area is scanned, in accordance with the irregularity of said surface at said elemental area so as to reduce to a negligible magnitude the effects of differences in said signals resulting from differences in the acoustical path lengths between said source and different elemental areas of said irregular surface scanned by said focussed acoustical energy, and forming a pattern of the modified signals.

6. The method of claim 5 wherein the pattern is a hologram produced by cooperation of the electrical signals and the electrical analog of a reference acoustical wave wherein the modification in accordance with the irregularities of the surface is effected by introducing into the electrical analog for each elemental area scanned, a phase shift determined by the irregularity of said elemental area.

7. The method of claim 6 wherein the phase shift for each elemental area is determined by the deviation of said elemental area from a hypothetical reference surface extending over the irregular surface.

8. The method of claim 7 wherein the reference surface is a hypothetical plane parallel to the plane traced by the focal point of the acoustic energy and passing through the point of the irregular surface which is nearest the scanning means.

9. The method of claim 7 wherein the resulting acoustic energy from flaws is received by acoustic energy receiving means, the said method including the preliminary steps of measuring the acoustic energy path-length between each elemental area scanned and the receiving means and determining the reference surface as the statistically best smooth surface defined by the measurements of the acoustic path lengths.

10. The method of claim 9 wherein the received acoustic energy is adjusted by suppressing from the formed pattern, signals received from scanned elemental areas of the irregular surface, whose deviation from signals received from scanned elemental areas of the reference surface exceeds a predetermined magnitude.

* * * * *